Figure 1:
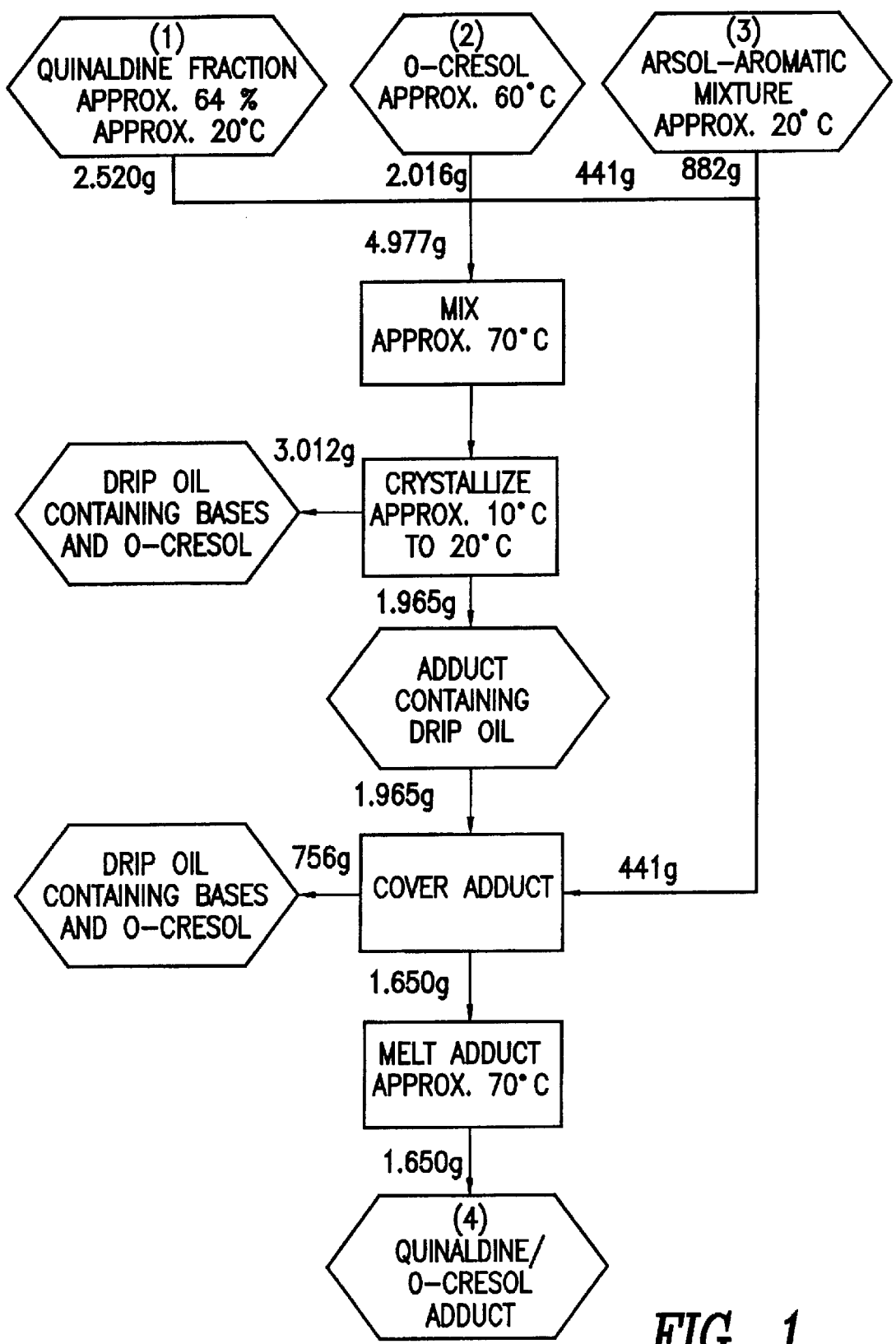

United States Patent [19]

Talbiersky et al.

[11] Patent Number: 6,020,494
[45] Date of Patent: Feb. 1, 2000

[54] METHOD OF PURIFYING QUINALDINE

[75] Inventors: Jörg Talbiersky, Dorsten; Edgar Fuhrmann, Castrop-Rauxel; Heinz-Günter Janneck, Datteln, all of Germany

[73] Assignee: Rutgers VFT AG, Germany

[21] Appl. No.: 09/104,637

[22] Filed: Jun. 25, 1998

[30] Foreign Application Priority Data

Jul. 5, 1997 [DE] Germany .................. 197 28 835

[51] Int. Cl.⁷ .................................................. C07D 215/04
[52] U.S. Cl. .................................................. 546/181
[58] Field of Search .................................................. 546/181

[56] References Cited

U.S. PATENT DOCUMENTS

| | | | |
|---|---|---|---|
| 4,081,351 | 3/1978 | Heinemann | 208/8 |
| 4,429,170 | 1/1984 | Lovell | 568/761 |
| 4,443,636 | 4/1984 | Greco | 568/761 |
| 4,583,990 | 4/1986 | McGarry | 44/51 |
| 4,656,279 | 4/1987 | Okazaki | 546/150 |

FOREIGN PATENT DOCUMENTS 736589  9/1955  United Kingdom .

OTHER PUBLICATIONS

Chemical Abstracts, 106:4899e, Separation and Purification of Quinaldine, 1987, based on JP 61 93,165.

*Primary Examiner*—D. Margaret Mach
*Attorney, Agent, or Firm*—Hedman, Gibson & Costigan, P.C.

[57] ABSTRACT

In a method of purifying quinaldine prepared from coal tar, a phenol, cresol and xylenol-type mononuclear aromatic compound is added to the quinaldine fraction, said aromatic compound is crystallized out forming an adduct with quinaldine and the quinaldine/mononuclear aromatic adduct is then separated, whereby, before the mononuclear aromatic compound is added, 5% to 20% by weight of a mixture of aromatic compounds or toluene, in relation to the mass of the quinaldine fraction, is added to the quinaldine fraction.

4 Claims, 2 Drawing Sheets

METHOD OF PURIFYING QUINALDINE

BACKGROUND, SUMMARY AND DESCRIPTION OF THE INVENTION

The invention concerns a method of purifying quinaldine, starting from a fraction of quinaldine from processed coal tar in which quinaldine is crystallized out with mononuclear aromatic compounds, an adduct is formed and the quinaldine/aromatic compound adduct is separated.

The stream of methyl naphthalene from processed coal tar that contains the quinaldine fraction contains various quinoline bases whose boiling points are very close to one another. Thus, 8-methyl quinoline has a boiling point of 247.75° C., 2-methyl quinoline (quinaldine) has a boiling point of 247.6° C. and isoquinoline has a boiling point of 243° C. Quinaldine is contained in this fraction in a concentration of about 60%; enrichment by distilling to qualities greater than 90% is not possible because of the byproducts of boiling, in particular 8-methyl quinoline.

From U.S. Pat. No. 2,432,064, it is known how to form an adduct of crude quinaldine with a mononuclear phenol that yields quinaldine qualities with a purity of 95% to 98%. However, it turns out that this method cannot be copied in a reproducible way.

The problem underlying the invention is providing a reproducible method of obtaining quinaldine in even greater purity than the known method and in a more reproducible way.

This problem is solved by using a method of purifying quinaldine in which a phenol, cresol and xylenol-type mononuclear aromatic compound is added to a quinaldine fraction prepared from coal tar, said aromatic compound is crystallized out forming an adduct with quinaldine and the quinaldine/mononuclear aromatic compound adduct is then separated and before the mononuclear aromatic compound is added, up to 20% by weight of an aromatic mixture (arsol) or toluene, in relation to the mass of the quinaldine fraction, is added to the quinaldine fraction.

As the raw material for obtaining high-purity quinaldine, a quinaldine fraction prepared from coal tar can be used that is obtained by distillation and contains, by weight, about 60% quinaldine.

According to a preferred embodiment of the invention 15 to 20% in particular about 18% by weight, based on the weight of the fraction containing quinaldine, of a toluene or arsol mixture is added to the fraction containing quinaldine.

In the invention, arsol-aromatic mixtures are understood as aromatic mixtures that may contain toluene, benzene, xylenes, ethyl benzenes, propyl benzenes, indan, indene, high-boiling compounds and other unidentified compounds. These aromatic mixtures occur, for example, as the base product in a xylene main column during crude benzene processing as arsol I, which boils between 165° C. and 180° C., and arsol II, which boils between 180° C. and 200° C.

After treatment with toluene or the arsol-aromatic mixture according to the invention, mononuclear aromatic compounds such as phenol, cresol and xylenol are added to form the adduct. o-Cresol, m-cresol and p-Cresol, as well as 3,4-xylenol and 2,4-xylenol, can be used. o-Cresol is especially preferred. According to another preferred embodiment of the invention, this o-Cresol is prepared from tar.

As is known, o-Cresol prepared from tar can have base contents of more than 1%. However, it is possible to use such qualities without disadvantages. Furthermore, it is surprising to note that in this case, when the described method is used, a high-percentage of practically base-free o-Cresol is produced. This possibility of refining o-Cresol containing bases increases the economic potential of the method in the invention, according to a preferred execution variant. The invention thus also concerns a method of removing bases prepared from o-Cresol from tar.

After the adduct is formed, the mixture is cooled to a temperature of 0 to 25° C., preferably from 10° C. to 25° C., and the adduct precipitates spontaneously from the mixture. Preferably, the mixture is precipitated in the crystallizer in EP 148 511 A2, in which the cool surfaces are placed at an angle of more than 0° to the vertical or horizontal. The liquid mixture crystallizing out is thus at rest or at most moves at a speed at which there are no crystals loosening from the cool surfaces and no crystals breaking off from the crystal layer.

The use of such a slanting-surface crystallizer facilitates a short crystallization distance and has the advantage of one-step crystallization.

The quinaldine/o-Cresol adduct has a relatively high melting point at about 65° C. The adduct is formed with high selectivity of 99.3% adduct purity, in relation to quinaldine/o-Cresol. The adduct can be split up thermally, and hence also by distillation into its basic components.

The quinaldine produced in a lab column has an average content of 98.7%, and 50% of that produced has a purity greater than 99%.

Furthermore, the o-Cresol can be recovered, with the exception of distillation losses, at a low boiling point from the mother liquor formed from the adduct. The o-Cresol from the adduct distillation has an average content of 99.5%, with a peak content of 99.9%, and can therefore be recycled for adduct formation or sold as a high-purity product.

The method in the invention will be explained in greater detail using the following example, but is not limited to it.

EXAMPLE

Production of 99% quinaldine by the o-Cresol adduct method 2,520 g 64% quinaldine fraction (1) are mixed at 20° C. with 441 g arsol-aromatic mixture (3) in a 10-liter glass beaker. Then 2,016 g o-Cresol prepared from tar (2) are added to the above solution. The solution is heated to about 70° C. by the reaction heat released. The entire mixture is cooled to 20° C. in a laboratory inclined-surface crystallizer for crystallization. The mother liquor is separated from the crystal product by dripping off, and the crystal product is washed with 441 g arsol-aromatic mixture. The washed crystal product (4), 1650 g, consists largely of o-Cresol, quinaldine and arsol-aromatic mixture. This crystal product is melted and separated in a 2 m laboratory column. (wire-mesh filler) by fractionating rectification. In this way, a low-base o-Cresol is obtained (>500 ppm bases) and a high-purity quinaldine (5), 790 g with a quinaldine content of about 99.4%.

DESCRIPTION OF FIGS. 1 AND 2

Figure 2:
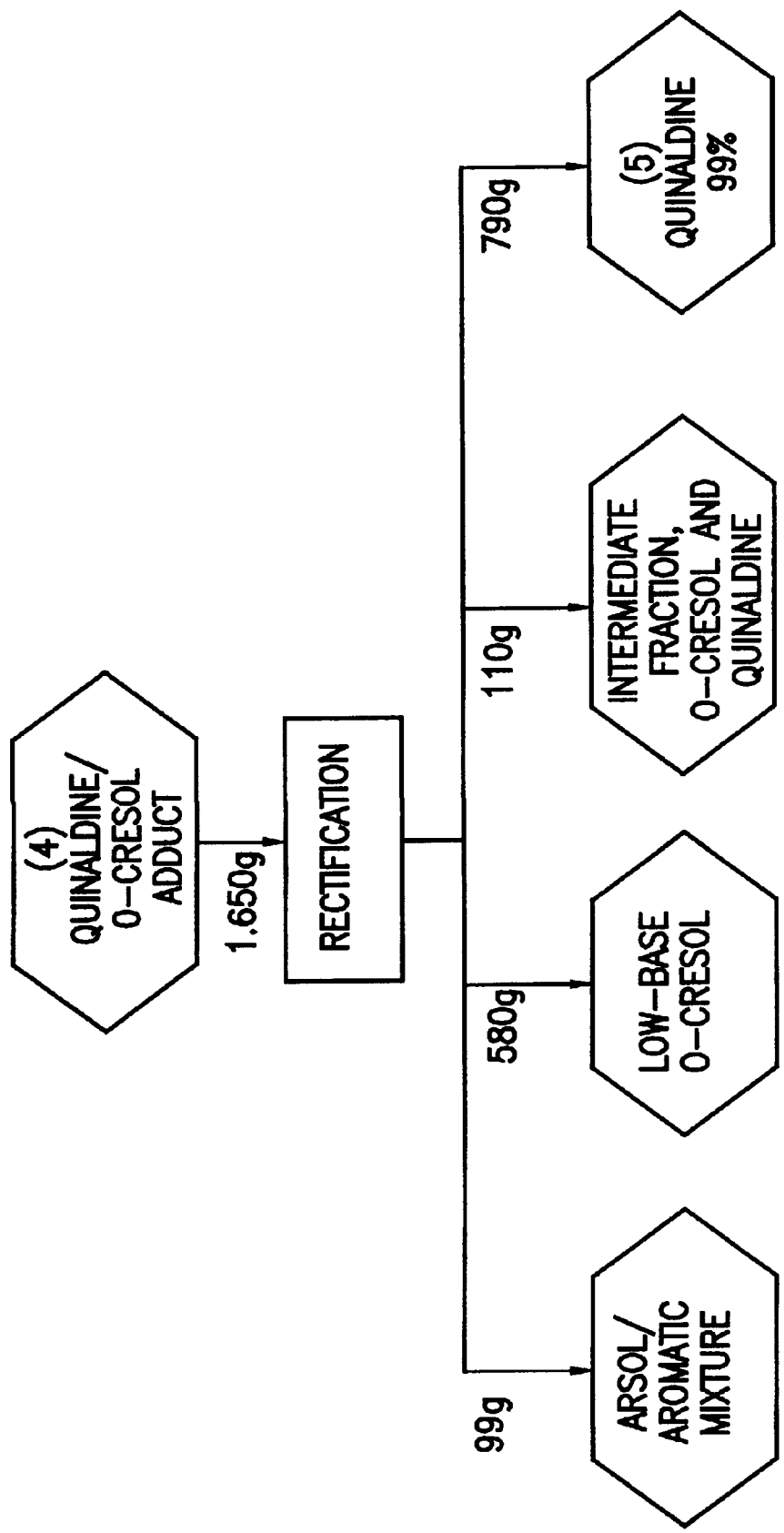

FIGS. 1 and 2 describe a preferred example of how to carry out the procedure. This is followed by the composition of the products and materials or mixture of materials added.

(1) Quinaldine Fraction (% Mass)

Low boilers 2%, quinoline<2%, isoquinoline 10–20%, quinaldine 60–70%, 8-methyl quinoline 5–10%, 3-methyl isoquinoline 3–8%, lepidine<5%, high boilers<10%.

(2) o-Cresol Composition (% Mass)

Phenol 0.5%, o-Cresol 98.2%, m/p cresol 0.5%, bases 0.8%.

(3) Arsol-aromatic Mixture (% Mass)

benzene 6%, toluene 8%, xylene 13%, ethyl benzene 3%, C3 benzene 34%, indan 14%, indene 6%, unidentified compounds 14%, high boilers 2%.

(4) Quinaldine/o-Cresol Adduct (% Mass)

BTX aromatic compounds 5.4%, o-Cresol 40.2%, isoquinoline 0.2%, unknown compounds 0.2% quinaldine 53.4%, 8-methyl quinoline 0.3%, 3-methyl isoquinoline 0.2%, lepidine 0.1%.

(5) Quinaldine 99% (% Mass)

Isoquinoline 0.05%, unknown compounds 0.1%, quinaldine 99.4%, 8-methyl quinoline 0.4%, 3-methyl isoquinoline 0.05%.

What we claims is:

1. A method of purifying quinaldine processed from coal tar said method comprising the following steps:

adding to a quinaldine fraction 5%–20% of toluene or an aromatic mixture comprising one or more of toluene, benzene, xylenes, ethyl benzenes, propyl benzenes, indan and indene, based on the mass of the quinaldine fraction, then adding to said mixture a phenol, cresol and/or xylenol mononuclear aromatic compound, and then crystallizing the quinaldine fraction from the quinaldine/mononuclear aromatic compound adduct.

2. The method of claim 1 wherein the adduct fromed from quinaldine and mononuclear aromatic compounds is crystallized out in a crystallizer in which the cool surfaces are arranged at an angle of more than 0° to the vertical or horizontal.

3. The method of claim 1, wherein the o-cresol mononuclear aromatic compound which used to form the adduct with quinaldine is an o-cresol prepared from a bases-containing coal.

4. A method of purifying quinaldine processed from coal tar said method comprising the following steps:

adding to a quinaldine fraction 5%–20% of toluene or an aromatic mixture comprising one or more of toluene, benzene, xylenes, ethyl benzenes, propyl benzenes, indan and indene, based on the mass of the quinaldine fraction, then adding to said mixture a mononuclear aromatic compound selected from phenol, cresol, xylenol and mixtures thereof to form a quinaldine/mononuclear aromatic compound adduct, and then crystallizing the quinaldine fraction from the quinaldine/mononuclear aromatic compound adduct.

* * * * *